United States Patent [19]

Wilk et al.

[11] Patent Number: 5,417,697
[45] Date of Patent: May 23, 1995

[54] POLYP RETRIEVAL ASSEMBLY WITH CAUTERIZATION LOOP AND SUCTION WEB

[76] Inventors: Peter J. Wilk, 185 W. End Ave., New York, N.Y. 10023; Cary W. Schneebaum, 230 Brinckerhoff Ct., Englewood, N.J. 07631

[21] Appl. No.: 219,148

[22] Filed: Mar. 29, 1994

Related U.S. Application Data

[63] Continuation-in-part of Ser. No. 88,831, Jul. 7, 1993.
[51] Int. Cl.⁶ .............................. A61B 17/39
[52] U.S. Cl. ........................ 606/113; 606/46; 606/115
[58] Field of Search .............. 606/1, 32, 34, 37, 41, 606/43, 45–50, 110–115, 205–209

[56] References Cited

U.S. PATENT DOCUMENTS

| | | |
|---|---|---|
| 4,557,255 | 10/1985 | Goodman . |
| 4,997,435 | 3/1991 | Demeter ..................... 606/127 |
| 5,084,054 | 1/1992 | Bencini et al. . |
| 5,147,371 | 9/1992 | Washington et al. . |
| 5,158,561 | 10/1992 | Rydell et al. . |
| 5,176,687 | 1/1993 | Hasson et al. . |
| 5,190,542 | 3/1993 | Nakao et al. . |
| 5,190,561 | 3/1993 | Graber ........................ 606/127 |
| 5,192,284 | 3/1993 | Pleatman . |
| 5,196,003 | 3/1993 | Bilweis . |
| 5,215,521 | 6/1993 | Cochran et al. . |
| 5,234,439 | 8/1993 | Wilk et al. . |
| 5,279,548 | 1/1994 | Essig et al. . |

FOREIGN PATENT DOCUMENTS

| | | |
|---|---|---|
| 0499243 | 8/1992 | European Pat. Off. . |
| 0537533 | 4/1993 | European Pat. Off. ............ 606/113 |
| 1683701 | 10/1991 | U.S.S.R. ........................... 606/113 |

*Primary Examiner*—Stephen C. Pellegrino
*Assistant Examiner*—Glenn Dawson
*Attorney, Agent, or Firm*—R. Neil Sudol; Henry D. Coleman

[57] ABSTRACT

A procedure for endoscopically removing a polyp utilizes an elongate tubular member having a cup-shaped web member at a distal end portion and an electrically conductive cauterization loop inserted through the tubular member. Upon insertion of an endoscope assembly into a patient, the distal end portion of the tubular member and the cauterization loop are ejected from the distal end of the biopsy channel of the endoscope assembly. Upon a subsequent opening of the cauterization loop, the cauterization loop is placed over a polyp to be removed, the web member is then opened and suction is applied through the tubular member to entrain the polyp to the web member. Electrical current is conducted to the cauterization loop to sever the polyp from the patient, and the loop is closed. The severed polyp is held in the web member by suction and is subsequently removed from the patient.

4 Claims, 4 Drawing Sheets

POLYP RETRIEVAL ASSEMBLY WITH CAUTERIZATION LOOP AND SUCTION WEB

This application is a continuation-in-part of application Ser. No. 08/088,831 filed Jul. 7, 1993, now pending.

BACKGROUND OF THE INVENTION

This invention relates to an endoscopic procedure for retrieving objects such as polyps from inside patients. This invention also relates to an associated endoscopic instrument assembly.

In a conventional polyp retrieval operation, an endoscope is inserted into an internal cavity of a patient, e.g., into the colon, and is used to visually identify and locate the polyp in the internal cavity. Upon the identification of the polyp or other growth which is to be removed, a wire extending through a tube in the biopsy channel of the endoscope is slid in the distal direction so that a cauterization loop connected to the wire is ejected from the distal end of the tube and the endoscope. The loop and the endoscope are manipulated from outside of the patient to pass the loop over the polyp or growth. The wire is then withdrawn in the proximal direction to tighten the loop around a base region or neck of the polyp. Once the loop is in contact with the base region of the polyp, an electrical current is conducted through the loop via the wire. Generally, as the loop is closed about the base region of the polyp, electrical current is transmitted through the narrowed organic tissues and thereby generates therein heat sufficiently great to cut and cauterize.

Once a polyp is severed by such a snare cauterization technique, it frequently becomes difficult to capture the polyp and retrieve it from the patient. Sometimes the cauterization loop is used in an effort to ensnare the polyp. Other capture techniques involve the use of forceps or the application of suction. In using forceps, the snare cauterization tube is removed from the biopsy channel of the endoscope and replaced with the forceps. In using suction, a vacuum is applied via a suction channel of the endoscope.

No matter which specific technique is used, the polyp frequently escapes from the capturing instrumentality and falls away into the colon (or other cavity). Especially in cases where the polyp is large, the effort and time expended in retrieving the severed polyp may rival or even exceed the effort and time required to locate and sever the polyp. In extreme cases, the endoscope must be removed without the polyp and the patient given an enema in an attempt to flush out the polyp from the colon.

Furthermore, there are numerous cases where a severed polyp is never recovered. Sometimes, the polyp is masserated during the retrieval attempt. In all such cases, the pathologist is unable to determine whether the polyp contains carcinoma in situ (localized) or infiltrative carcinoma (spread). The patient must then undergo a colon ressection, sometimes unnecessarily.

In any event, the manipulations necessary to remove a severed polyp generally increase the trauma to the patient, the expense of the surgery and the hospitalization time. There is now a long-felt need to improve the snare cauterization technique to facilitate the capture and retrieval of severed polyps.

U.S. Pat. Nos. 5,201,740 and 5,190,542 to Nakao and Wilk disclose a cauterization loop with an attached capture pocket. Such a snare assembly represents a significant advance in the art and evidently solves all of the problems inherent in polyp retrieval. However, it appears that there is some rooom in the industry for an alternative method for snare retrieval.

OBJECTS OF THE INVENTION

An object of the present invention is to provide a method for the removal of portions of internal body organs or other objects from patients.

A more specific object of the present invention is to provide such a method which may be used in conjunction with snare cauterization operations.

Another object of the present invention is to provide a technique wherein the capture and retrieval of severed polyps is facilitated.

Another, more particular, object of the present invention is to provide a polyp retrieval technique wherein trauma to the patient and time in surgery are reduced.

A further object of the present invention is to provide an instrument assembly for use in removing portions of body organs or other objects from patients.

Yet another, more particular, object of the present invention is to provide such an instrument assembly which facilitates the capture and retrieval of severed polyps and other clumps of severed body tissues from the internal cavities of patients.

Another particular object of the present invention is to provide such an instrument assembly which is simple to manufacture and therefore inexpensive.

A further particular object of the present invention is to provide such an instrument assembly which is easy to use.

An additional particular object of the present invention is to provide such an instrument assembly which is disposable. Such an instrument assembly requires no lengthy sterilization procedure and reduces the spread of infectious diseases such as AIDS.

These and other objects will be apparent from the following descriptions.

SUMMARY OF THE INVENTION

A surgical instrument comprises, in accordance with the present invention, an elongate tubular member having a flexible distal end portion, and an electrically conductive cauterization loop connected to the tubular member along an outer surface of the distal end portion so that the loop is coextensive with the distal end portion.

According to another feature of the present invention, the surgical instrument further comprises a capture device slidably inserted through the tubular member. The capture device may be a loop member provided with a capture pocket and attached to a distal end of an elongate member inserted through the tubular member. Alternatively, the capture component may be a Dormia basket or a web member having a substantially cup-shaped opened configuration with a concave inner surface.

According to another feature of the present invention, the loop includes a first portion connected along its length to the tubular member and a second portion connected only at opposite ends to the tubular member. The first portion of the cauterization loop may be partially embedded along its length in the tubular member. The embedding is not so extensive as to interfere with snare cauterization operations.

The distal end portion of the tubular member is advantageously provided with an inherent spring bias tending to form that distal end portion into an arcuate configuration. In addition, the first and the second portion of the cauterization loop may have an inherent spring bias tending to form the loop into an opened configuration.

The surgical device is to be used largely in endoscopic snare cauterization procedures. Accordingly, the tubular member has an external dimension sufficiently small so that the tubular member is insertable through a biopsy channel of an endoscope.

An associated surgical method in accordance with the present invention utilizes a device as described above, i.e., an elongate tubular member having a distal end portion and an electrically conductive cauterization loop connected to the tubular member along an outer surface of the distal end portion so that the cauterization loop is substantially coextensive with the distal end portion. The method comprises the steps of (a) inserting an endoscope assembly into a patient, the endoscope assembly having a biopsy channel with a distal end, (b) ejecting the distal end portion of the tubular member and the cauterization loop from the distal end of the biopsy channel of the endoscope assembly upon insertion of the endoscope assembly into the patient, (c) opening the cauterization loop from a collapsed configuration to an opened configuration upon ejection of the cauterization loop from the biopsy channel, (d) upon the opening of the cauterization loop, maneuvering the endoscope assembly and the cauterization loop from outside the patient to place the cauterization loop over a polyp to be removed, and (e) upon placement of the cauterization loop over the polyp, conducting electrical current to the cauterization loop to sever the polyp from the patient.

According to a further feature of the present invention, the method further comprises the steps of (f) providing a capture device, (g) ejecting the capture device from the tubular member upon ejection of the tubular member from the biopsy channel, and (h) engaging the polyp with the capture device upon severing of the polyp from the patient to entrain the polyp for removal from the patient. As discussed above, the capture device may be a loop member provided with a capture pocket, a Dormia basket or a web member having a substantially cup-shaped opened configuration with a concave inner surface. In any case, the method also comprises the step of expanding the capture device from a collapsed configuration to an opened operative configuration upon ejection of the capture device from the tubular member and prior to the engaging of the polyp with the capture device.

The opening of the cauterization loop may be implemented automatically upon ejection of the tubular member and the cauterization loop from the biopsy channel of the endoscope, at least partially by virtue of an inherent spring bias of the distal end portion of the tubular member.

A surgical instrument assembly comprises, in accordance with an alternate form of the present invention, an elongate tubular member insertable through a biopsy channel of an endoscope, the tubular member being provided at a distal end with a web member having a cup shape defining a concave inner surface. A cauterization snare member is inserted through the tubular member so that a cauterization loop at a distal end of the snare member is ejectable from the distal end of the tubular member. A connector or other component is provided on said tubular member, at a proximal end thereof, for enabling application of suction to the web member via the tubular member to generate a negative pressure at the inner surface upon an ejection of the web member from the biopsy channel of the endoscope and upon an opening of the web member from a collapsed configuration to the cup shape.

According to an additional feature of the present invention, the surgical instrument assembly further comprises spreading elements operatively connected to the web member for automatically opening the web member from the collapsed configuration to the cup shape upon an ejection of the web member from the biopsy channel of the endoscope. The spreading elements may include a plurality of ribs having a spring bias tending to open the web member from the collapsed configuration to the cup shape.

A method for removing an polyp from inside a patient in accordance with the present invention utilizes a surgical device including an elongate tubular member having, at a distal end, a web member with a cup shape defining a concave inner surface. This method also utilizes a cauterization snare member insertable through the tubular member so that a cauterization loop at a distal end of the snare member is ejectable from the distal of the tubular member. This method comprises the steps of (i) inserting an endoscope assembly into a patient, the endoscope assembly having a biopsy channel with a distal end, (ii) pushing the tubular member through the biopsy channel so that the web member is ejected from the distal end of the biopsy channel, (iii) opening the web member from a collapsed configuration to an opened configuration upon ejection of the web member from the biopsy channel, (iv) also upon insertion of the endoscope assembly into the patient, shifting the snare member through the tubular member so that the cauterization loop is ejected from the tubular member, (v) opening the cauterization loop from a collapsed configuration to an opened configuration upon ejection of the cauterization loop from the tubular member, (vi) maneuvering the ejected cauterization loop from outside the patient to place the cauterization loop over a polyp to be removed, (vii) conducting electrical current to the placed cauterization loop to sever the polyp from the patient, (viii) during the conducting of current, shifting the cauterization loop and the tubular member relative to one another so that the cauterization loop is drawn back into the tubular member and closes about a portion of the polyp to sever the polyp, and (ix) applying suction through the tubular member to generate a vacuum force between the web member and the severed polyp to thereby entrain the severed polyp to the tubular member.

In a method in accordance with the present invention, the capture and retrieval of severed polyps is facilitated. An instrument assembly in accordance with the present invention is simple to use. Accordingly, trauma to the patient and time in surgery are reduced. More specifically, time under anaesthesia with the accompanying side effects is reduced. Concomitantly, the expense of hospitalization is decreased.

DETAILED DESCRIPTION

Figure 1:
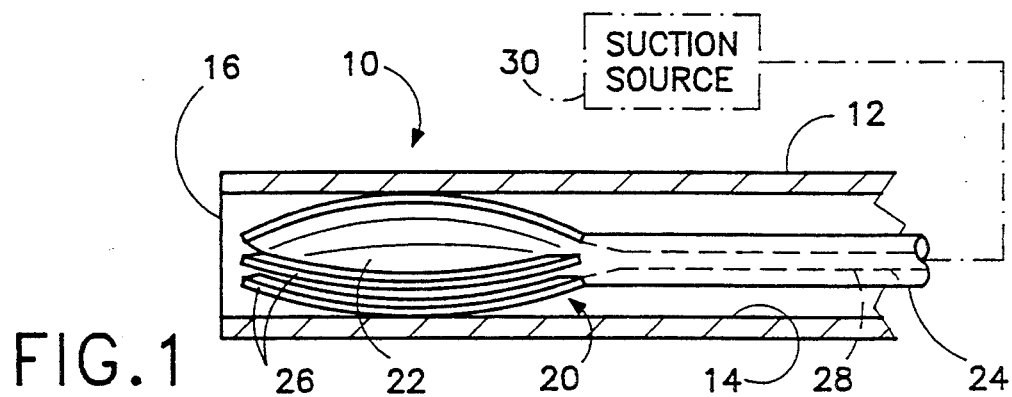
FIG. 1 is a partial schematic longitudinal cross-sectional view, on a substantially enlarged scale, of an endoscopic polyp retrieval device in accordance with the present invention, showing a cup-shaped web member in a collapsed configuration.
Figure 2:
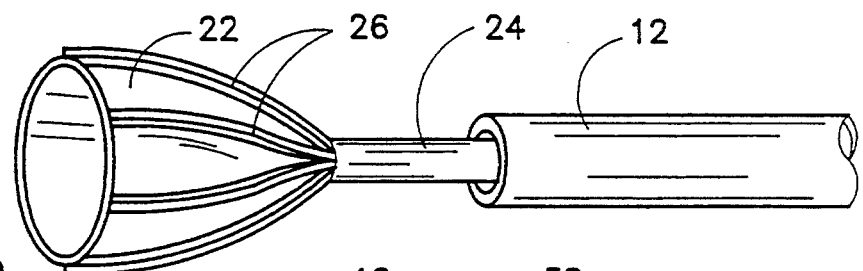
FIG. 2 is a partial schematic side perspective view of the endoscopic polyp retrieval device of FIG. 1, showing the web member in an opened configuration.

As illustrated in FIGS. 1 and 2, an endoscopic polyp retrieval device 10 comprises a tubular member 12 defining a tubular endoscopic channel 14. Tubular member 12 may be an endoscope insertion member, while endoscopic channel is a biopsy channel of the endoscope. Alternatively, tubular member 12 may be a separate instrument insertable into a biopsy channel of an endoscope.

Endoscopic channel 14 has a distal end 16. A capture component 20 is slidably disposed in tubular endoscopic channel 14. Capture component 20 includes a web member 22 disposed in a collapsed configuration inside channel 14. Web member or membrane 22 is attached at a distal end to a flexible rod 24. A plurality of longitudinally extending ribs 26 are attached to web member 22. Ribs 26 all have an internal spring bias tending to spread web member 22 into a cup-shaped opened configuration (FIG. 2) upon an ejection of the web member from tubular member 12 under the action of a distally directed stroke of rod 24.

Optionally, rod 24 is hollow, as indicated at 28, and is operatively connected at a proximal end to a suction source or vacuum pump 30, whereby web member 22 may be subjected, on a concave side, to a vacuum underpressure tending to hold an entrained object in the web member.

To remove a severed polyp PO (FIG. 3A) from inside a colon CN of a patient, an endoscope insertion member 32 is inserted into the colon. Endoscope insertion member 32 includes a fiber optic illumination guide and a fiber optic image guide represented by an illumination outlet port 34 and an imaging window 36, respectively. Endoscope insertion member 32 is further provided with a biopsy channel 38 in which tubular member 12 is slidably inserted.

Figure 3A:
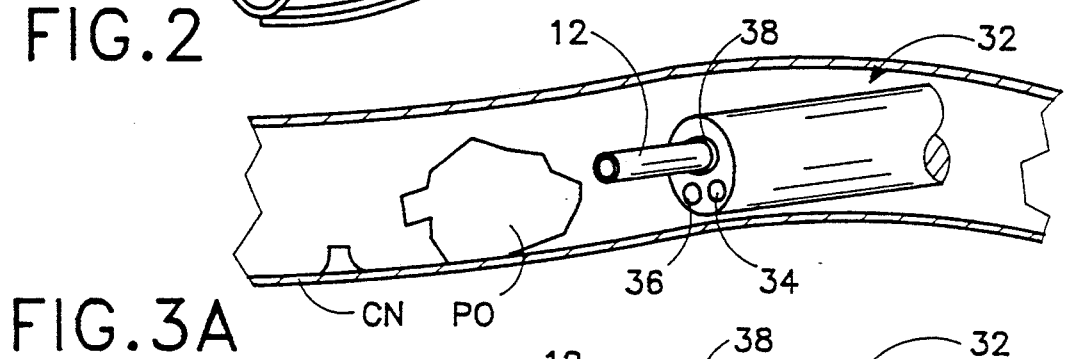
FIGS. 3A–3C are schematic partial perspective views of an endoscopic polyp retrieval assembly and partially cross-sectional views of a patient's colon, showing successive steps in the use of the device of FIGS. 1 and 2 in conjunction with an endoscope.
Figure 3B:
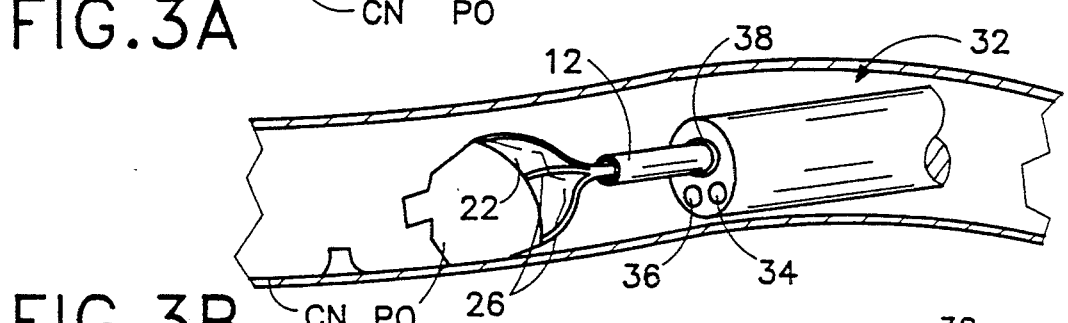
Figure 3C:
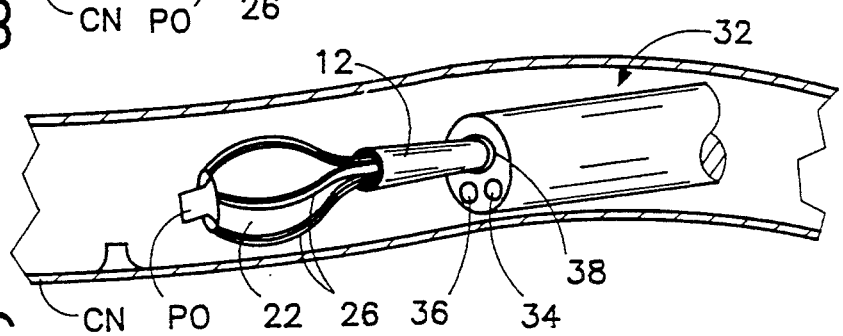

Upon the detection of polyp PO via illumination outlet port 34 and imaging window 36, tubular member 12 is pushed in a distal direction to emerge from biopsy channel 36, as illustrated in FIG. 3A. Subsequently, rod 24 (FIGS. 1 and 2) is shifted distally to eject web member 22 from channel 14. Under the action of ribs 26, web member 22 expands to the opened configuration of FIG. 2. Then endoscope insertion member 32, as well as retrieval device 10, is manipulated from outside the patient to bring the opened web member 22 into such juxtaposition with polyp PO that the polyp is inserted through a mouth of the web member and into the web member, as illustrated in FIGS. 3B and 3C. At that juncture, tubular member 12 is shifted in the distal direction to engage web member 22 and ribs 26 and to partially close the web member about the captured polyp PO, thereby effectively locking the polyp in the web member. Endoscope insertion member 32 and retrieval device 10, together with the entrained polyp PO, are removed from colon CN.

The clamping of polyp PO by ribs 26 and web member 22 under the camming closure action of tubular member 12 may be supplemented by the application of suction to the space between an inner concave surface of cup-shaped web member 22 and polyp PO. A consequent vacuum or underpressure tends to hold polyp PO to or inside web member 22 during the withdrawal of endoscope insertion member 32 from colon CN.

It is to be noted that the vacuum or negative pressure generated inside web member 22 by suction source 30 may be used exclusively to retain polyp PO in web member 22. In that event, tubular member 12 is not shifted forward to close ribs 26 and web member 22. Indeed, tubular member 12 may be omitted altogether, in which case capture component 20 is inserted directly through biopsy channel 36 without the tubular member.

Figure 4:
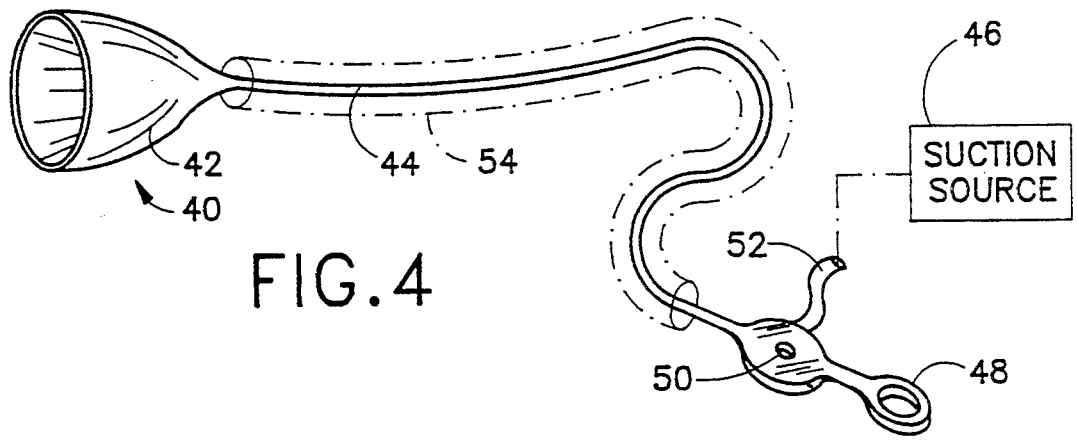
FIG. 4 a schematic perspective view of an endoscopic polyp retrieval device for use with an endoscope in an endoscopic polyp retrieval procedure in accordance with the present invention.

FIG. 4 depicts an endoscopic polyp retrieval device 40 having a web member 42 at a distal end, a tubular shaft 44, and a suction source or vacuum generator 46 at a proximal end. The endoscopic polyp retrieval device 40 is further provided at the proximal end with a handgrip 48 for facilitating the alternate pushing and pulling of tubular shaft 44 and with an aperture 50 in a suction line 52, for enabling a user to use his or her thumb to close the pneumatic circuit extending from vacuum generator 46 to web member 42. Endoscopic polyp retrieval device 40 is insertable through a tubular member 54, which is either an endoscope insertion member or a tubular member itself insertable through an endoscope biopsy channel.

Figure 5A:
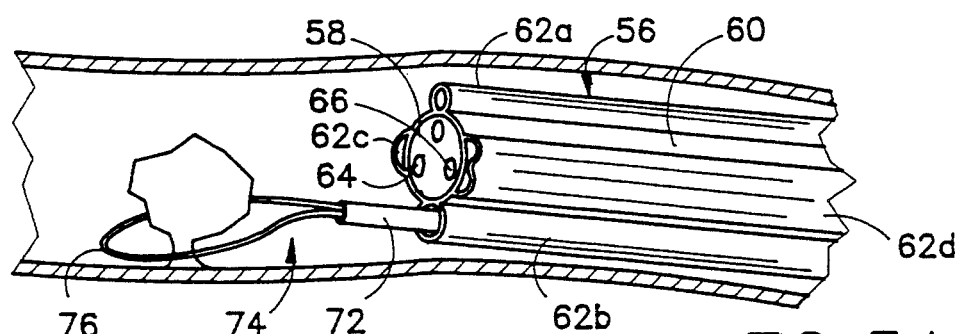
FIGS. 5A–5C are partially partial perspective views of an endoscopic polyp retrieval assembly and partially cross-sectional views of a patient's colon, showing successive steps in a polyp retrieval procedure.

As illustrated in FIG. 5A, an endoscopic polyp retrieval assesmbly 56 comprises an endoscope insertion member 58 surrounded by a sheath 60 having a plurality of expandable biopsy channels 62a, 62b, 62c, 62d. Such a sheath is described and illustrated in U.S. Pat. No. 5,217,001 the disclosure of which is hereby incorporated by reference. Endoscope insertion member 58 also has a fiber optic illumination guide 64 and a fiber optic image guide 66.

A tubular member 68 of a endoscopic polyp retrieval device 70 (FIG. 5B) is inserted through one biopsy channel 62a, while a tubular member 72 of a cauterization snare 74 is inserted through another biopsy channel 62b. Upon the locating of a polyp POL via an image guide 66, tubular member 72 of snare 74 is pushed in the distal direction so that a distal end portion of the instrument emerges from biopsy channel 62b, as illustrated in FIG. 5A. At that juncture, a cauterization loop 76 (FIG. 5A) is ejected from a folded configuration inside tubular member 72. Endoscope insertion member 58 and tubular member 72 are then manipulated from outside the patient so as to place cauterization loop 76 over polyp POL.

Figure 5B:
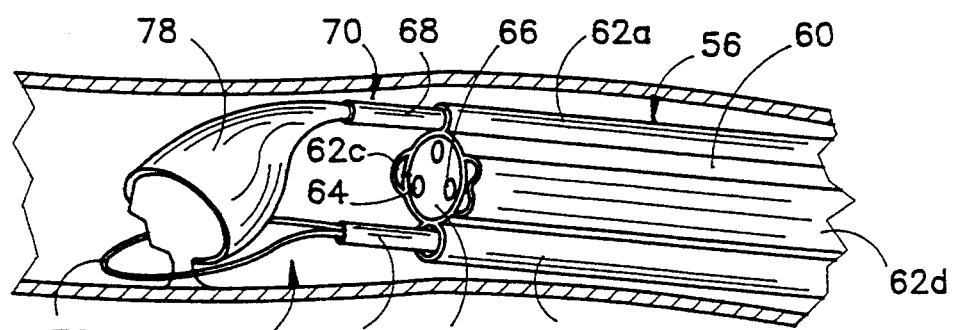

Upon the placement of cauterization loop 76 over polyp POL, tubular member 68 is shifted distally so as to partially emerge from biopsy channel 62a, as illustrated in FIG. 5B. A web member 78 is ejected from tubular member 68, opened and moved to a position in juxtaposition or engagement with polyp POL. At that point suction is applied to web member 78 to secure polyp POL to the web member, as discussed hereinabove.

Figure 5C:
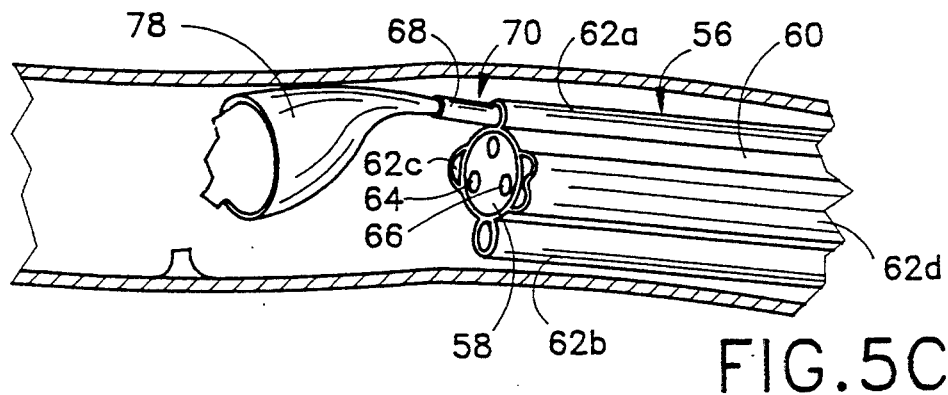

Upon the securing of polyp POL to web member 78, tubular member 72 is shifted further in the distal direction to collapse cauterization loop 76 about the base of polyp POL. Electrical current is conducted to cauterization loop 76, pursuant to conventional techniques, whereupon polyp POL is severed, as indicated in FIG. 5C. The severed polyp POL is entrained to web member 78 via suction and may be removed from the colon CLN with endoscope insertion member 58.

It is to be noted that the endoscopic polyp retrieval device embodiment of FIGS. 1 and 2 may be used in the endoscope assembly of FIGS. 5A-5C, whereby the web member can be closed through a camming action, as discussed above, either with or without the application of suction. In any case, web member 78 is provided with ribs (not designated) for facilitating the automatic opening of the web member upon ejection thereof from tubular member 68.

Figure 6A:
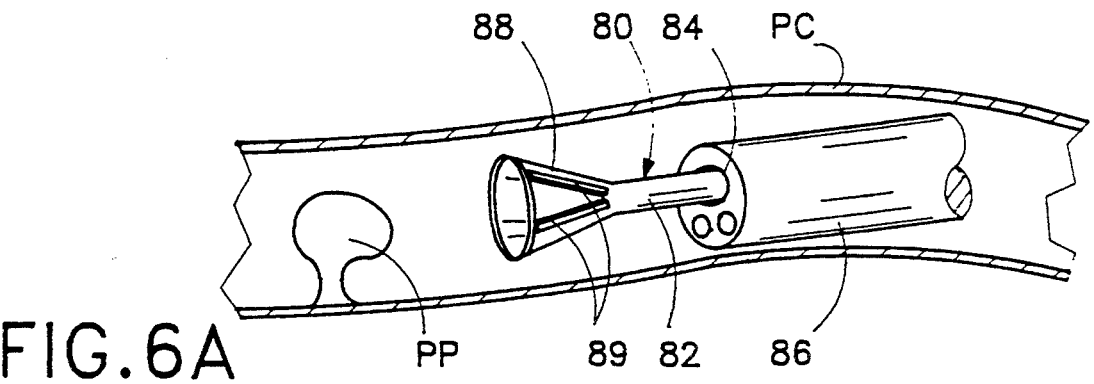
FIGS. 6A–6C are partially partial perspective views of another endoscopic polyp retrieval assembly and partially cross-sectional views of a patient's colon, showing successive steps in a polyp retrieval procedure in accordance with the present invention.
Figure 6B:
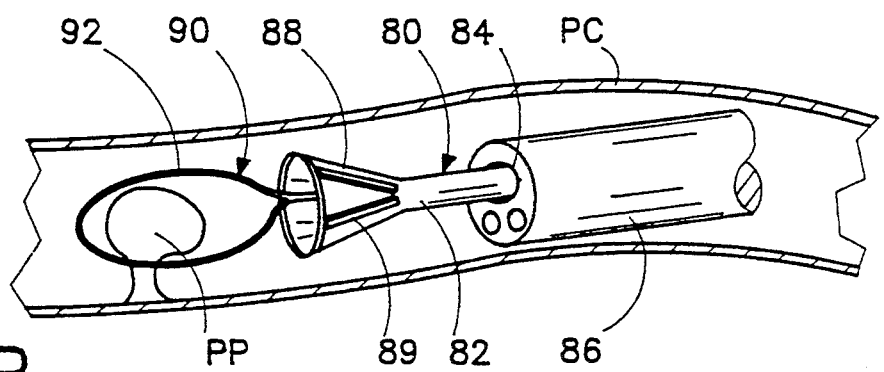
Figure 6C:
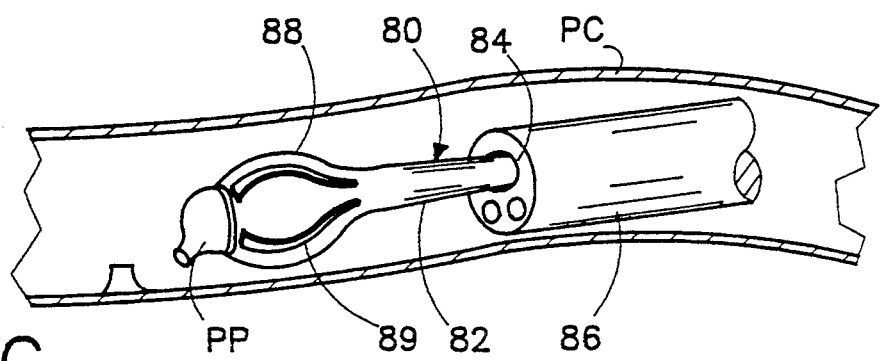

As illustrated in FIGS. 6A-6C, a method for removing an polyp PP from inside a patient's colon PC utilizes an endoscopic surgical device 80 including an elongate tubular member 82 insertable through a biopsy channel 84 of a flexible endoscope insertion member 86. Tubular member 82 is provided at a distal end with a cup-shaped web member 88 defining a concave inner surface (not designated). The endoscope surgical device 80 also includes a cauterization snare member 90 insertable through tubular member 82 so that a cauterization loop 92 at a distal end of the snare member is ejectable from the distal end of tubular member 82, through the opened web member 88.

Upon insertion of endoscope insertion member 86 into colon PC, tubular member 82 is pushed through biopsy channel 84 so that web member 88 is ejected from the distal end of the biopsy channel. Web member 88 is then opened from a collapsed insertion configuration to an opened configuration, as shown in FIG. 6A. In addition, following insertion of endoscope insertion member 86 into colon PC, snare member 90 is shifted through tubular member 82 so that cauterization loop 92 is ejected from the tubular member. Upon ejection from tubular member 82, cauterization loop 92 automatically expands from a collapsed configuration inside the tubular member to an opened configuration, as illustrated in FIG. 6B. The opening or expansion of loop 92 is implemented by virtue of an inherent spring bias or memory shape which tends to open the loop.

Upon ejection of cauterization loop 92 from tubular member 82, the ejected loop is maneuvered from outside the patient to place the loop over polyp PP, as shown in FIG. 6B. Electrical current is conducting to the placed cauterization loop 92 to sever polyp PP from the patient. During the conducting of electrical current, cauterization loop 92 and tubular member 82 are shifted relative to one another so that cauterization loop 92 is drawn back into tubular member 82 and closes about a portion of polyp PP to thereby sever the polyp. Suction is applied through tubular member 82 to generate a vacuum force between web member 88 and the severed polyp PP to thereby entrain the severed polyp to the tubular member, as illustrated in FIG. 6C.

Figure 7A:
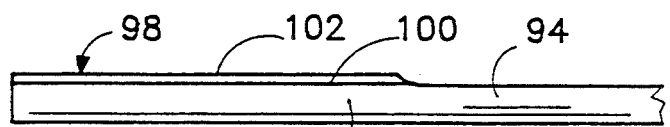
FIG. 7A is a partial schematic longitudinal side elevational view, on an enlarged scale, of an endoscopic cauterization snare device in accordance with the present invention, showing the device in a colapsed, insertion configuration.
Figure 7B:
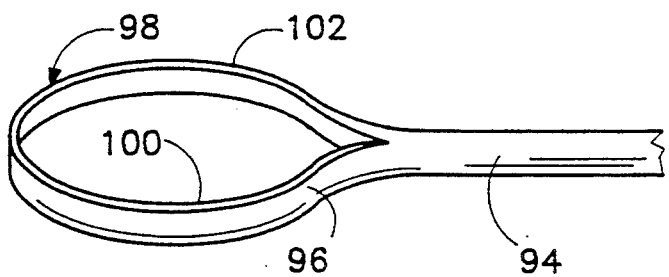
FIG. 7B is a side elevational view similar to FIG. 7A, showing the cauterization snare device in in an expanded or opened, use configuration.

As depicted in FIGS. 7A and 7B, a surgical instrument comprises an elongate tubular member 94 having a flexible distal end portion 96. An electrically conductive cauterization loop 98 is connected to tubular member 94 along an outer surface of distal end portion 96 so that loop 98 is substantially coextensive with distal end portion 96. Loop 98 includes a first portion 100 connected along its length to tubular member 94 and a second portion 102 connected only at opposite ends to tubular member 94. The one portion 100 of cauterization loop 98 may be partially embedded along its length in tubular member 94. The embedding is limited so as not to interfere with snare cauterization operation.

Distal end portion 96 of tubular member 94 is provided with an inherent spring bias tending to form that distal end portion into an arcuate use configuration, as illustrated in FIG. 7B. In addition, first and second portions 100 and 102 of cauterization loop 98 may have an inherent spring bias tending to form the loop into an opened configuration (FIG. 7B).

Figure 8A:
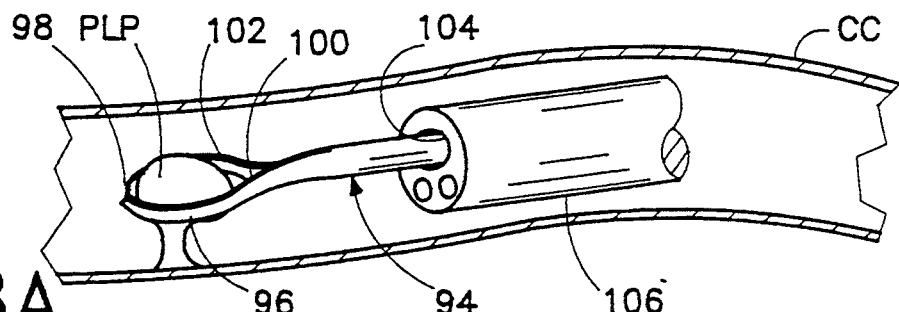
FIGS. 8A–8C are schematic partial perspective views of an endoscopic polyp retrieval assembly and partially cross-sectional views of a patient's colon, showing successive steps in the use of the device of FIGS. 7A and 7B in conjunction with an endoscope.

As illustrated in FIG. 8A, tubular member 94 is inserted through a biopsy channel 104 of an endoscope insertion member 106 and pushed through the biopsy channel so that disal end portion 96 and loop 98 are ejected from the biopsy channel upon deployment of insertion member 106 in a colon CC of a patient. Upon ejection from biopsy channel 104, distal end portion 96 changes from the straightened insertion configuration of FIG. 7A to the arcuate use configuration of FIG. 7B. In addition, cauterization loop 98 opens from the collapsed configuration of FIG. 7A to the expanded configuration of FIG. 7B.

Figure 8B:
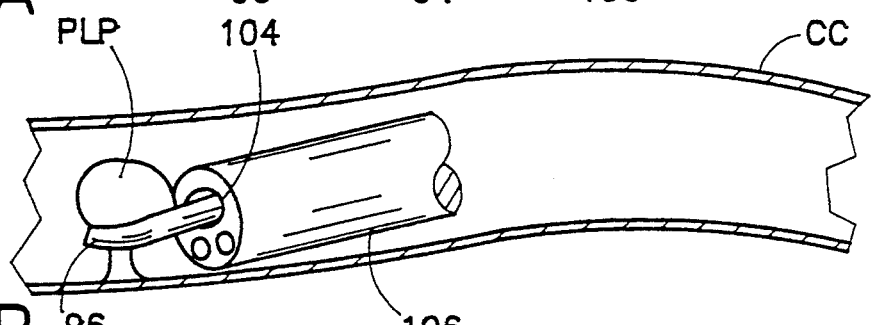

Upon the opening of cauterization loop 98, endoscope insertion member 106 and tubular member 94 are manipulated from outside the patient to place the cauterization loop over a polyp PLP to be removed from the wall of colon CC (FIG. 8A). Upon placement of cauterization loop 98 over polyp PLP, as shown in FIG. 8B, electrical current is conducted to the cauterization loop to sever the polyp from the patient. Simultaneously, distal end portion 96 and endoscope insertion member 106 are shifted towards one another to retract the distal end portion of tubular member 94 and cauterization loop 98 back into biopsy channel 104, thereby closing the loop about polyp PLP and completing the severing thereof. It is to be noted that an additional tubular member (not shown) may be provided about tubular member 94 and inside biopsy channel 104.

Figure 8C:
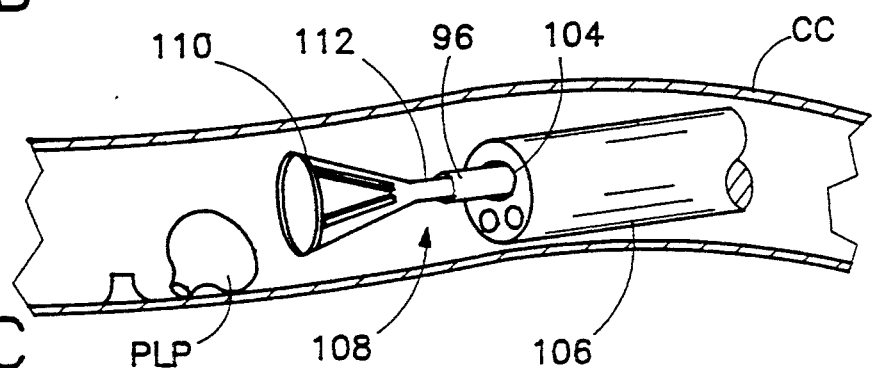

As depicted in FIG. 8C, a capture device 108 exemplarily in the form of a cup- or cone-shaped web member 110 at the distal end of a tubular member 112 is ejected from tubular member 94 upon the severing of polyp PLP. Web member 110 is similar in structure and function to the web member illustrated in FIGS. 1 and 2 and the web member of FIGS. 6A–6C. Suction is applied via tubular member 112 to attach web member 110 to the severed polyp PLP via a vacuum lock. Polyp PLP is engaged with web member 110 to entrain the polyp for removal from the patient.

Figure 9:
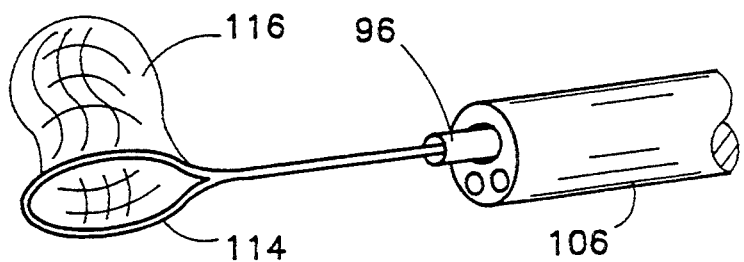
FIG. 9 is a schematic perspective view, showing a modified endoscopic polyp retrieval assembly for alternative use in the step illustrated in FIG. 8C.
Figure 10:
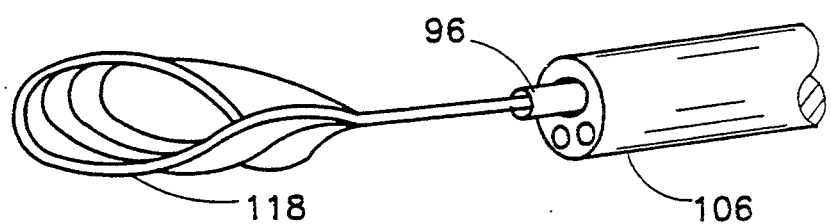
FIG. 10 is a schematic perspective view, showing another modified endoscopic polyp retrieval assembly for alternative use in the step of FIG. 8C.

As illustrated in FIG. 9, the capture device may take the form of a loop member 114 provided with a capture pocket 116. FIG. 10 shows a capture device in the form of a Dormia basket 118. In any case, the capture device is slidably inserted through tubular member 94 and expanded from a collapsed insertion configuration to an opened operative configuration upon ejection from the tubular member and prior to engagement with polyp PLP.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A surgical instrument assembly comprising:
   an elongate tubular member insertable through a biopsy channel of an endoscope, said tubular member being provided at a distal end with a web member having a cup shape defining a concave inner surface;
   a cauterization snare member inserted through said tubular member so that a cauterization loop at a distal end of said snare member is ejectable from the distal end of said tubular member; and
   means operatively connected to said tubular member for enabling application of suction to said web member to generate a negative pressure at said inner surface upon an ejection of said web member from the biopsy channel of the endoscope and upon an opening of said web member from a collapsed configuration to said cup shape.

2. The assembly defined in claim 1, further comprising spreading means operatively connected to said web member for automatically opening said web member from said collapsed configuration to said cup shape upon an ejection of said web member from the biopsy channel of the endoscope.

3. The assembly defined in claim 2 wherein said spreading means includes a plurality of ribs attached to said web member, said ribs having a spring bias tending to open said web member from said collapsed configuration to said cup shape.

4. A method for removing an polyp from inside a patient, comprising the steps of:
   providing a surgical device including an elongate tubular member having, at a distal end, a web member with a cup shape defining a concave inner surface;
   also providing a cauterization snare member insertable through said tubular member so that a cauterization loop at a distal end of said snare member is ejectable from the distal of said tubular member;
   inserting an endoscope assembly into a patient, said endoscope assembly having a biopsy channel with a distal end;
   upon insertion of said endoscope assembly into the patient, pushing said tubular member through said biopsy channel so that said web member is ejected from the distal end of the biopsy channel;
   opening said web member from a collapsed configuration to an opened configuration upon ejection of said web member from said biopsy channel;
   also upon insertion of said endoscope assembly into the patient, shifting said snare member through said tubular member so that said cauterization loop is ejected from said tubular member;
   opening said cauterization loop from a collapsed configuration to an opened configuration upon ejection of said cauterization loop from said tubular member;
   upon the opening of said cauterization loop, maneuvering said cauterization loop from outside the patient to place said cauterization loop over a polyp to be removed;
   upon placement of said cauterization loop over the polyp, conducting electrical current to said cauterization loop to sever said polyp from the patient;
   during said step of conducting, shifting said cauterization loop and said tubular member relative to one another so that said cauterization loop is drawn back into said tubular member and closes about a portion of the polyp to sever the polyp;
   applying suction through said tubular member to generate a vacuum force between said web member and the severed polyp to thereby entrain the severed polyp to the tubular member and removing said tubular member with the entrained severed polyp from the patient.

* * * * *